(12) United States Patent
Staniforth et al.

(10) Patent No.: US 9,566,239 B2
(45) Date of Patent: *Feb. 14, 2017

(54) PHARMACEUTICAL FORMULATIONS FOR DRY POWDER INHALERS

(71) Applicant: VECTURA LIMITED, Chippenham (GB)

(72) Inventors: John Nicholas Staniforth, Bath (GB); David Alexander Vodden Morton, Bath (GB); Rajbir Gill, Wiltshire (GB); Gaetano Brambilla, Parma (IT); Rossella Musa, Parma (IT); Lorenzo Ferrarini, Parma (IT)

(73) Assignee: VECTURA LIMITED, Chippenham, Wiltshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/492,156

(22) Filed: Sep. 22, 2014

(65) Prior Publication Data

US 2015/0050350 A1 Feb. 19, 2015

Related U.S. Application Data

(63) Continuation of application No. 12/386,758, filed on Apr. 21, 2009, now Pat. No. 8,871,274, which is a continuation of application No. 10/257,886, filed as application No. PCT/GB01/01751 on Apr. 17, 2001, now Pat. No. 7,541,022.

(30) Foreign Application Priority Data

Apr. 17, 2000 (GB) .................................... 0009469.8
Jun. 27, 2000 (EP) .................................... 00113608

(51) Int. Cl.
| | | |
|---|---|---|
| A61K 9/16 | (2006.01) | |
| A61K 9/00 | (2006.01) | |
| A61K 9/14 | (2006.01) | |
| A61K 31/167 | (2006.01) | |
| A61K 31/58 | (2006.01) | |

(52) U.S. Cl.
CPC .............. *A61K 9/16* (2013.01); *A61K 9/0075* (2013.01); *A61K 9/145* (2013.01); *A61K 9/1682* (2013.01); *A61K 31/167* (2013.01); *A61K 31/58* (2013.01)

(58) Field of Classification Search
CPC ........ A61K 9/16; A61K 9/0075; A61K 9/145; A61K 31/167; A61K 31/58; A61K 9/1682
See application file for complete search history.

(56) References Cited

U.S. PATENT DOCUMENTS

| | | |
|---|---|---|
| 1,242,211 A | 10/1917 | Raymond et al. |
| 5,376,386 A | 12/1994 | Ganderton et al. |
| 5,478,578 A | 12/1995 | Arnold et al. |
| 5,506,203 A | 4/1996 | Backstrom et al. |
| 6,153,224 A | 11/2000 | Staniforth |
| 6,475,523 B1 | 11/2002 | Staniforth |
| 6,521,260 B1 | 2/2003 | Staniforth |
| 6,528,096 B1 | 3/2003 | Musa et al. |
| 6,641,844 B1 | 11/2003 | Musa et al. |
| 6,645,466 B1 | 11/2003 | Keller et al. |
| 6,884,794 B2 | 4/2005 | Staniforth et al. |
| 7,541,022 B2 | 6/2009 | Staniforth et al. |
| 7,744,855 B2 | 6/2010 | Staniforth et al. |
| 8,101,160 B2 * | 1/2012 | Staniforth ............ A61K 9/0075 424/45 |
| 8,182,791 B2 * | 5/2012 | Staniforth ............ A61K 9/0075 128/200.14 |
| 8,871,274 B2 * | 10/2014 | Staniforth ...................... 424/46 |
| 2003/0162835 A1 | 8/2003 | Staniforth et al. |
| 2003/0165436 A1 | 9/2003 | Staniforth et al. |
| 2003/0175214 A1 | 9/2003 | Staniforth et al. |
| 2003/0180227 A1 | 9/2003 | Staniforth et al. |
| 2004/0037785 A1 | 2/2004 | Staniforth et al. |
| 2004/0047810 A1 | 3/2004 | Staniforth et al. |
| 2004/0071635 A1 | 4/2004 | Staniforth et al. |

(Continued)

FOREIGN PATENT DOCUMENTS

| | | |
|---|---|---|
| AU | 703924 | 4/1999 |
| CA | 2347856 | 2/2009 |

(Continued)

OTHER PUBLICATIONS

Magnesium Stearate, in Kibbe AH et al (1999) Handbook of Pharmaceutical Excipients (3rd Edition), Pharmaceutical Press, London, pp. 305-308.
A. E. Hawkins "The Shape of Poser-Particle Outlines", Research Studies Press Ltd., England 1993.
Hallworth et al., J. Pharm Pharmacol, vol. 39, 1987, pp. 966-972.
Zeng et al. "Particulate Interactions in Dry Powder Formulations for Inhalation" Taylor & Francis, London and New York, 2001, pp. 165-167.
The Merck Index, Eleventh Edition, Merck & Co., Inc., U.S.A. 1989, p. 843.
Zeng et al. "Particulate Interactions in Dry Powder Formulations for Inhalation" Taylor & Francis, London and New York, 2001, pp. 220-224.
Expert Report of Professor Graham Buckton dated Mar. 22, 2012.
Experimental report entitled "Contact Angle Analysis of Lactose/Magnesium Stearate Mixtures by Various Methods" dated Aug. 28, 2009.

(Continued)

*Primary Examiner* — Mina Haghighatian
(74) *Attorney, Agent, or Firm* — Matthew S. Gibson; Reed Smith LLP

(57) ABSTRACT

A powder for use in a dry powder inhaler comprises: i) a fraction of fine particle size constituted by a mixture of physiologically acceptable excipient and an additive; ii) a fraction of coarse particles; and iii) at least one active ingredient. The powder is suitable for efficacious delivery of active ingredients into the low respiratory tract of patients suffering from pulmonary diseases such as asthma. In particular, the invention provides a formulation to be administered as dry powder for inhalation which is freely flowable, can be produced in a simple way, is physically and chemically stable and capable of delivering accurate doses and/or high fine particle fraction of low strength active ingredients by using a high- or medium resistance device.

22 Claims, No Drawings

(56) References Cited

U.S. PATENT DOCUMENTS

| 2005/0152849 A1 | 7/2005 | Staniforth |
| 2006/0147389 A1 | 7/2006 | Staniforth et al. |

FOREIGN PATENT DOCUMENTS

| CA | 2406119 | 7/2009 |
| EP | 0441740 | 1/1991 |
| EP | 0663815 | 12/1992 |
| GB | 1242211 | 8/1967 |
| GB | 1381872 | 6/1971 |
| GB | 1520247 | 8/1978 |
| GB | 1571629 | 11/1997 |
| WO | 8705213 | 2/1987 |
| WO | 9511666 | 5/1995 |
| WO | 9524889 | 9/1995 |
| WO | 9623485 | 1/1996 |
| WO | 9602231 | 2/1996 |
| WO | 9703649 | 2/1997 |
| WO | 9831351 | 1/1998 |
| WO | 9831353 | 7/1998 |
| WO | 0028979 | 5/2000 |
| WO | 0033789 | 6/2000 |
| WO | 0053157 | 9/2000 |
| WO | 0178693 | 10/2001 |

OTHER PUBLICATIONS

Excerpt of N.M. Kassem (1990) "Generation of deeply inspirable clouds from dry powder mixtures" University of London.

D. Ganderton "The Generation of Respirable Clouds Form Coarse Powder Aggregates" Journal of Biopharmaceutical Sciences 3: 1-2; 101-105 (1992).

Y. Kawashima et al. "Effect of surface morphology of carrier lactose on dry powder inhalation property of pranlukast hydrate" International Journal of Pharmaceutics 172; 179-188 (1998).

F. Podczeck "The Influence of Particle Size Distribution and Surface Roughness of Carrier Particles on the in vitro Properties of Dry Powder Inhalations" Aerosol Science and Technology 31; 301-312 (1999).

Cassie, A.B.D. et al. Wettability of Porous Surfaces, Jun. 19, 1994, pp. 546-551.

Hancock, Bruno C. et al., Characteristics and Significance of the Amorphous State in Pharmaceutical Systems, Journal of Pharm Sci., vol. 86, No. 1, pp. 1-12, Jan. 1997.

Green. "Studies on Co-Micronization of Small Excipient and Small Additive Particles." Experimental Report. Vectura. Dec. 16, 2013.

Cassie. A.B.D. et al. Wettability of Porous Surfaces, Jun. 19, 1944 pp. 546-551.

* cited by examiner

PHARMACEUTICAL FORMULATIONS FOR DRY POWDER INHALERS

The present application is a continuation of still pending U.S. application Ser. No. 12/386,758, filed Apr. 21, 2009, which is a continuation application of U.S. application Ser. No. 10/257,886, filed Jun. 2, 2003, now issued U.S. Pat. No. 7,541,022, which is the United States national stage of International Application No. PCT/GB01/01751 filed Apr. 17, 2001, and which claims benefit of Great Britain Patent Application No. 0009469.8, filed Apr. 17, 2000 and European Patent Application No. 00113608.4, filed Jun. 27, 2000, the entire contents of which are incorporated herein by reference, including any references cited therein.

The invention relates to a formulation to be administered as dry powder for inhalation suitable for efficacious delivery of active ingredients into the low respiratory tract of patients suffering of pulmonary diseases such as asthma.

PRIOR ART

Inhalation anti-asthmatics are widely used in the treatment of reversible airway obstruction, inflammation and hyperresponsiveness.

Presently, the most widely used systems for inhalation therapy are the pressurised metered dose inhalers (MDIs) which use a propellant to expel droplets containing the pharmaceutical product to the respiratory tract.

However, despite their practicality and popularity, MDIs have some disadvantages:
i) droplets leaving the actuator orifice could be large or have an extremely high velocity resulting in extensive oropharyngeal deposition to the detriment of the dose which penetrates into the lungs;
the amount of drug which penetrates the bronchial tree may be further reduced by poor inhalation technique, due to the common difficulty of the patient to synchronise actuation form the device with inspiration;
ii) chlorofluorocarbons (CFCs), such as freons contained as propellants in MDIs, are disadvantageous on environmental grounds as they have a proven damaging effect on the atmospheric ozone layer.

Dry powder inhalers (DPIs) constitute a valid alternative to MDIs for the administration of drugs to airways. The main advantages of DPIs are:
i) being breath-actuated delivery systems, they do not require co-ordination of actuation since release of the drug is dependent on the patient own inhalation;
ii) they do not contain propellants acting as environmental hazards;
iii) the velocity of the delivered particles is the same or lower than that of the flow of inspired air, so making them more prone to follow the air flow than the faster moving MDI particles, thereby reducing upper respiratory tract deposition.

DPIs can be divided into two basic types:
i) single dose inhalers, for the administration of pre-subdivided single doses of the active compound;
ii) multidose dry powder inhalers (MDPIs), either with pre-subdivided single doses or pre-loaded with quantities of active ingredient sufficient for multiple doses; each dose is created by a metering unit within the inhaler.
On the basis of the required inspiratory flow rates (l/min) which in turn are strictly depending on their design and mechanical features, DPI's are also divided in:

i) low-resistance devices (>90 l/min);
ii) medium-resistance devices (about 60 l/min);
iii) high-resistance devices (about 30 l/min).

The reported flow rates refer to the pressure drop of 4 KPa (KiloPascal) in accordance to the European Pharmacopoeia (Eur Ph).

Drugs intended for inhalation as dry powders should be used in the form of micronised powder so they are characterised by particles of few microns (µm) particle size. Said size is quantified by measuring a characteristic equivalent sphere diameter, known as aerodynamic diameter, which indicates the capability of the particles of being transported suspended in an air stream. Hereinafter, we consider as particle size the mass median aerodynamic diameter (MMAD). Respirable particles are generally considered to be those with diameters from 0.5 to 6 µm, as they are capable of penetrating into the lower lungs, ie the bronchiolar and alveolar sites, where absorption takes place. Larger particles are mostly deposited in the oropharyngeal cavity so they cannot reach said sites, whereas the smaller ones are exhaled.

Although micronisation of the active drug is essential for deposition into the lower lungs during inhalation, it is also known that the finer are the particles, the stronger are the cohesion forces. Strong cohesion forces hinder the handling of the powder during the manufacturing process (pouring, filling). Moreover they reduce the flowability of the particles while favouring the agglomeration and/or adhesion thereof to the walls. In multidose DPI's, said phenomena impair the loading of the powder from the reservoir to the aerosolization chamber, so giving rise to handling and metering accuracy problems.

Poor flowability is also detrimental to the respirable fraction of the delivered dose, the active particles being unable to leave the inhaler and remaining adhered to the interior of the inhaler, or leaving the inhaler as large agglomerates; agglomerated particles, in turn, cannot reach the bronchiolar and alveolar sites of the lungs. The uncertainty as to the extent of agglomeration of the particles between each actuation of the inhaler and also between inhalers and different batches of particles, leads to poor dose reproducibility as well.

In the prior art, one possible method of improving the flowing properties of these powders is to agglomerate, in a controlled manner, the micronised particles to form spheres of relatively high density and compactness. The process is termed spheronisation while the round particles formed are called pellets. When, before spheronisation, the active ingredient is mixed with a plurality of fine particles of one or more excipients, the resulting product has been termed as soft pellets.

Otherwise powders for inhalation could be formulated by mixing the micronised drug with a carrier material (generally lactose, preferably α-lactose monohydrate) consisting of coarser particles to give rise to so-called 'ordered mixtures'.

However, either ordered mixtures and pellets should be able to effectively release the drug particles during inhalation, in order to allow them to reach the target site into the lungs.

In this regard, it is well known that the interparticle forces which occur between the two ingredients in the ordered mixtures may turn out to be too high thus preventing the separation of the micronised drug particles from the surface of the coarse carrier ones during inhalation. The surface of the carrier particles is, indeed, not smooth but has asperities and clefts, which are high energy sites on which the active particles are preferably attracted to and adhere more strongly. In addition, ordered mixtures consisting of low strength active ingredients could also face problems of uniformity of distribution and hence of metering accurate doses.

On the other hand, soft pellets may reach a so high internal coherence as to compromise their breaking up into the small particles during inhalation; such drawback could be regarded as a particular critical step when high-resistance dry powder inhalers are used. With said inhalers, less energy is indeed available for breaking up the pellets into the small primary particles of the active ingredient. The soft pellets may also face some problems of handling during filling and use of the inhalers.

In consideration of all problems and disadvantages outlined, it would be highly advantageous to provide a formulation aimed at delivering low strength active ingredients after inhalation with a DPI device, preferably a high-resistance one and exhibiting: i) good uniformity of distribution of the active ingredient; ii) small drug dosage variation (in other words, adequate accuracy of the delivered doses); iii) good flowability; iv) adequate physical stability in the device before use; v) good performance in terms of emitted dose and fine particle fraction (respirable fraction).

Another requirement for an acceptable formulation is its adequate shelf-life.

It is known that the chemical compounds can undergo chemico-physical alterations such as amorphisation, when subjected to mechanical stresses. Amorphous or partially amorphous materials, in turn, absorb water in larger amounts than crystalline ones (Hancock et al. *J. Pharm. Sci.* 1997, 86, 1-12) so formulations containing active ingredients, whose chemical stability is particularly sensitive*to the humidity content, will benefit during their preparation by the use of as low as possible energy step treatment.

Therefore, it would be highly advantageous to provide a process for preparing said formulation in which a low energy step is envisioned during the incorporation of the active ingredient to the mixture in such a way. to ensure adequate shelf life of the formulation suitable for commercial distribution, storage and use.

OBJECT OF THE INVENTION

It is an object of the invention to provide a formulation to be administered as dry powder for inhalation suitable for efficacious delivery of active ingredients into the low respiratory tract of patients suffering from pulmonary diseases such as asthma. In particular, it is an object of the invention to provide a formulation to be administered as dry powder for inhalation which is freely flowable, can be produced in a simple way, physically and chemically stable and is capable of delivering accurate doses and/or high fine particle fraction of active ingredients.

According to a first embodiment of the invention there is provided a powder for use in a dry powder inhaler comprising: i) a fraction of fine particle size constituted of a mixture of a physiologically acceptable excipient and an additive, the mixture having a mean particle size of less than 35 µm; ii) a fraction of coarse particles constituted of a physiologically acceptable carrier having a particle size of at least 90 µm; and iii) at least one active ingredient, said mixture (i) being composed of up to 99% by weight of particles of the excipient and at least 1% by weight of additive and the ratio between the fine excipient particles and the coarse carrier particles being between 1:99 and 40:60% by weight.

In a preferred embodiment of the invention, the fraction (i) is prepared in such a way that the additive particles are attached on the surface of the excipient particles. Said feature, in turn, can be achieved either by co-micronising the excipient particles and the additive particles or by mixing the excipient particles in the micronised form and the additive particles in a Turbula or a high energy mixer.

Suitable mixers for carrying out a high energy mixing step in the context of such formulations are high shear mixers. Such mixers are known to those skilled in the art, and include, for example, the Cyclomix and the Mechano-Fusion mixers manufactured by Hosokawa Micron. It will be appreciated by those skilled in the art that other suitable apparatus or use in a high energy mixing step will include, for example, ball mills and jet mills, provided that the equipment and conditions are so arranged to provide the desired high energy mixing.

In one particular embodiment of the invention, the additive material particles partially coat the surface of the excipient particles and/or the coarse carrier particles. That may be achieved in the case of certain water-insoluble additives such as in particular magnesium stearate and other stearic esters, stearic acid, and other fatty acids and esters by exploiting their peculiar film forming properties as also reported in International Specification WO 00/53157. The coating can be established by scanning electron microscope and the degree of coating can be evaluated by means of image analysis methods.

It is preferable that the additive particles should, at least partially, coat the surface of both the excipient and the coarse carrier particles.

It has been found that the particle, size of the physiologically acceptable excipient; the main component of the mixture (i) is of particular importance and that the best results in terms of aerosol performances are achieved when its particle size is less than 35 µm, preferably less than 30, more preferably less than 20, even more preferably less than 15 µm.

In a more preferred embodiment, the formulation of the invention is in the form of 'hard pellets' and they are obtained by subjecting the mixture to a spheronisation process.

By the term 'hard pellets' we mean spherical or semi-spherical units whose core is made of coarse particles. The term has been coined for distinguishing the formulation of the invention from the soft pellets of the prior art which are constituted of only microfine particles (WO 95/24889, GB 1520247, WO 98/31353).

By the term 'spheronisation' we mean the process of rounding off of the particles which occurs during the treatment.

In an even more preferred embodiment of the invention, the coarse carrier particles have a particle size of at least 175 µm as well as a highly fissured surface. A carrier of the above mentioned particle size is particularly advantageous when the fine excipient particles constitute at least 10% by weight of the final formulation. It has been found that, whereas formulations containing conventional carriers and having fine particle contents of above 5% tend to have poor flow properties, and above 10% tend to have very poor flow properties, the formulations according to that preferred embodiment of the invention have adequate flow properties even at fines contents (that is contents of active particles and of fine excipient particles) of up to 40% by weight.

The prior art discloses several approaches for improving the flowability properties and the respiratory performances of low strength active ingredients. WO 98/31351 claims a dry powder composition comprising formoterol and a carrier substance, both of which are in finely divided form wherein the formulation has a poured bulk density of from 0.28 to 0.38 g/ml. Said formulation is in the form of soft pellet and does not contain any additive.

EP 441740 claims a process and apparatus thereof for agglomerating and metering non-flowable powders preferably constituted of micronised formoterol fumarate and fine particles of lactose (soft pellets).

Furthermore several methods of the prior art were generally addressed at improving the flowability of powders for inhalation and/or reducing the adhesion between the drug particles and the carrier particles.

GB 1,242,211, GB 1,381,872 and GB 1,571,629 disclose pharmaceutical powders for the inhalatory use in which the micronised drug (0.01-10 µm) is respectively mixed with carrier particles of sizes 30 to 80 µm, 80 to 150 µm, and less than 400 µm wherein at least 50% by weight of which is above 30 µm.

WO 87/05213 describes a carrier, comprising a conglomerate of a solid water-soluble carrier and a lubricant, preferably 1% magnesium stearate, for improving the technological properties of the powder in such a way as to remedy to the reproducibility problems encountered after the repeated use of a high resistance inhaler device.

WO 96/02231 claims a mixture characterised in that the micronised active compound is mixed with rough carrier particles having a particle size of 400 µm to 1000 µm. According to a preferred embodiment of the invention, the components are mixed until the carrier crystals are coated with the fine particles (maximum for 45 minutes). No example either with auxiliary additives and/or with low strength active ingredient is reported.

EP 0,663,815 claims the addition of finer particles (<10 µm) to coarser carrier particles (>20 µm) for controlling and optimising the amount of delivered drug during the aerosolisation phase.

WO 95/11666 describes a process for modifying the surface properties of the carrier particles by dislodging any asperities in the form of small grains without substantially changing the size of the particles. Said preliminary handling of the carrier causes the micronised drug particles to be subjected to weaker interparticle adhesion forces.

In WO 96/23485, carrier particles are mixed with an anti-adherent or anti-friction material consisting of one or more compounds selected from amino acids (preferably leucine); phospholipids or surfactants; the amount of additive and the process of mixing are preferably chosen in such a way as to not give rise to a real coating. The inventor believes that the presence of a discontinuous covering as opposed to a "coating" is an important and advantageous feature. The carrier particles blended with the additive are preferably subjected to the process disclosed in WO 95/11666.

Kassem (London University Thesis 1990) disclosed the use of relatively high amount of magnesium stearate (1.5%) for increasing the 'respirable' fraction. However, the reported amount is too great and reduces the mechanical stability of the mixture before use.

WO 00/28979, which was published after the earliest priority date of this application, describes the use of small amounts of magnesium stearate for improving stability to humidity of dry powder formulations for inhalation.

WO 00/33789, also published after the earliest priority date of this application, describes an excipient powder for inhalable drugs comprising a coarse first fraction, a fine second fraction, and a ternary agent which may be leucine.

In none of aforementioned documents the features of the formulation of the invention are disclosed and none of the teaching therein disclosed contributes to the solution of the problem according to the invention. All the attempts of obtaining stable powder formulations of low strength active ingredients endowed of good flowability and high fine particle fraction according to some of the teaching of the prior art, for example by preparation of ordered mixture, addition of a fine fraction, mere addition of additives, were indeed unsuccessful as demonstrated by the examples reported below. In particular, in the prior art it often occurred that the solutions proposed for a technical problem (ie improving dispersion of the drug particles) was detrimental to the solution of another one (ie improving flowability, mechanical stability) or vice versa. On the contrary, the formulation of the invention shows either excellent rheological properties and physical stability and good performances in terms of fine particle fraction, preferably more than 40%. The cohesiveness between the partners has been indeed adjusted in such a way as to give sufficient adhesion force to hold the active particles to the surface of the carrier particles during manufacturing of the dry powder and in the delivery device before use, but to allow the effective dispersion of the active particles in the respiratory tract even in the presence of a poor turbulence as that created by high-resistance devices.

Contrary to what has been stated in the prior art (EP 441740), in the formulation of the invention the presence of an additive does not necessarily compromise the integrity of the pellets before use.

According to a second embodiment of the invention there are also provided a process for making the formulation of the invention, in such a way that the additive particles partially coat the surface of either the excipient particles and the coarse carrier particles.

According to a particular embodiment, there is provided a process including the steps of: i) co-micronising the excipient particles and the additive particles so as to reduce their particle size below 35 µm, and contemporaneously making the additive particles partially coat the surface of the excipient particles; ii) spheronising by mixing the resulting mixture with the coarse carrier particles such that mixture particles adhere to the surface of the coarse carrier particles; iii) adding by mixing the active particles to the spheronised particles.

According to a further particular embodiment of the invention there is provided another process, said process including the steps of: i) mixing the excipient particles in the micronised form and the additive particles in such a way as to make the additive particles partially coat the surface of the excipient particles; ii) spheronising by mixing the resulting mixture with the coarse carrier particles such that mixture particles adhere to the surface of the coarse carrier particles; iii) adding by mixing the active particles to the spheronised particles.

When the coarse carrier particles have a particle size of at least 175 µm and in a preferred embodiment a highly fissured surface, the formulation of the invention could also be prepared by: i) co-mixing the coarse carrier particles, magnesium stearate and the fine excipient particles; ii) adding by mixing the active particles to the mixture.

It has been indeed found advantageous in some cases for the particles to be processed for at least two hours, to have a good fine particle fraction (respirable fraction) and no problem of sticking during the preparation.

Contrary to the prior art (WO 98/31351), the active ingredient may be incorporated in the-mixture by simple mixing so avoiding any potential mechanical stress which may disturb the crystallinity of its particles.

Advantageously, the coarse and fine carrier particles may be constituted of any pharmacologically acceptable inert material or combination thereof; preferred carriers are those made of crystalline sugars, in particular lactose; the most preferred are those made of a-lactose monohydrate. Advantageously the diameter of the coarse carrier particles is at least 100 μm, more advantageously at least 145 μm, preferably at least 175 μm, more preferably between 175 and 400 μm, even more preferably between 210 and 355 μm.

A number of methods may be used to determine whether carrier particles have such a fissured surface, which will offer the capability of retaining relatively large fines contents substantially without segregation:

1. Determination of tapped density.

The tapped density of the fissured carrier particles may be about 6% or more, and preferably 15% or more, lower than the tapped density of carrier particles of the same material and of particle characteristics of a kind typical of carrier particles which have conventionally been used in the manufacture of inhalable powders. In the case of fissured carrier particles of crystalline sugars, for example lactose, the tapped density of the fissured particles is not more than 0.75 $g/cm^3$, and preferably not more than 0.70 $g/cm^3$. The tapped density of lactose grades conventionally used in the manufacture of commercial DPI formulations is typically about 0.8 $g/cm^3$. Tapped densities referred to herein may be measured as follows:

A measuring cylinder is weighed on a top pan balance (2 place). Approximately 50 g powder is introduced into the measuring cylinder, and the weight is recorded. The measuring cylinder containing the powder is attached to a jolting volumeter (Jel Stampfvolumeter). The jolting volumeter is set to tap 200 times. During each tap, the measuring cylinder is raised and allowed to fall a set distance. After the 200 taps, the volume of the powder is measured. The tapping is repeated and the new volume measured. The tapping is continued until the powder will settle no more. The tapped density is calculated as the weight of the powder divided by the final tap volume. The procedure is performed three times (with new powder each time) for each powder measured, and the mean tapped density calculated from those three final tapped volume values.

2. Mercury Intrusion Porosimetry. Mercury intrusion porosimetry assesses the pore size distribution and the nature of the surface and pore structure of the particles. Porosimetry data is suitably collected over pressure range 3.2 kPa to 8.7 MPa, for example, using an Autopore 9200 II Porosimeter (Micromeritics, Norcross, USA). Samples should be evacuated to below 5 Pa prior to analysis to remove air and loosely bound surface water. Suitable lactose is characterised by a bulk density of not more than 0.65 $g/cm^3$ and preferably not more than 0.6 $g/cm^3$. Suitable lactose is also characterised by a total intrusion volume, as measured by mercury intrusion porosimetry, of at least 0.8 $cm^3g^{-1}$ and preferably at least 0.9 $cm^3g^{-1}$. (It has been found that lactose having a bulk density of 0.6 $g/cm^3$ as measured by mercury intrusion porosimetry has a tapped density of about 0.7 g/cm', whereas the discrepancy between the two methods at lower densities is less.)

3. "Fissure Index". The term "fissure index" used herein refers to the ratio of a theoretical envelope volume of the particles, as calculated from the envelope of the particles, to the actual volume of the particles, that is, omitting fissures within the envelope. Suitable particles are those having a fissure index of at least 1.25. The theoretical envelope volume may be determined optically, for example, by examining a small sample of the particles using an electron microscope. The theoretical envelope volume of the particles may be estimated via the following method. An electron micrograph of the sample may be divided into a number of grid squares of approximately equal populations, each containing a representative sample of the particles. The population of one or more grids may then be examined and the envelope encompassing each of the particles determined visually as follows. The Feret's diameter for particles within a grid is measured relative to a fixed axis of the image. Typically at least ten particles are measured for their Feret's diameter. Feret's diameter is defined as the length of the projection of a particle along a given reference line as the distance between the extreme left and right tangents that are perpendicular to the reference line. A mean Feret's diameter is derived. A theoretical mean envelope volume may then be calculated from this mean diameter to give a representative value for all the grid squares and thus the whole sample. Division of that value by the number of particles gives the mean value per particle. The actual volume of the particles may then be calculated as follows. First, the mean mass of a particle is calculated. A sample of approximately 50 mg is taken and its precise weight recorded to 0.1 mg. Then by optical microscopy the precise number of particles in that sample is determined. The mean mass of one particle can then be determined. The procedure is then repeated five times to obtain a mean value of this mean. Second, a fixed mass of particles (typically 50 g), is weighed out accurately, and the number of particles within this mass is calculated using the above mean mass value of one particle. Finally, the sample of particles is immersed in a liquid in which the particles are insoluble and, after agitation to remove trapped air, the amount of liquid displaced is measured. From this the mean actual volume of one particle can be calculated. The fissure index is advantageously not less than 1.5, and is, for example, 2 or more.

4. "Rugosity Coefficient". The rugosity coefficient is used to mean the ratio of the perimeter of a particle outline to the perimeter of the 'convex hull'. This measure has been used to express the lack of smoothness in the particle outline. The 'convex hull' is defined as a minimum enveloping boundary fitted to a particle outline that is nowhere concave. (See "The Shape of Powder-Particle Outlines" A. E. Hawkins, Wiley.) The 'rugosity coefficient' may be calculated optically as follows. A sample of particles should be identified from an electron micrograph as identified above. For each particle the perimeter of the particle outline and the associated perimeter of the 'convex hull' is measured to provide the rugosity coefficient. This should be repeated for at least ten particles to obtain a mean value. The mean rugosity coefficient is at least 1.25.

Carrier particles which have the above-mentioned capability of retaining relatively large amounts of fine material without or with only little segregation will generally' comply with all of Methods 1 to 4 above, but for the avoidance of doubt any carrier particles which comply with at least one of Methods 1 to 4 is deemed to be a fissured particle.

The additive material, which is preferably on the surfaces of the carrier particles, promotes the release of the active particles from the carrier particles on actuation of the inhaler device. The formulation containing the additive material should, however, be such that the active particles are not liable to be released form the carrier particles before actuation of the inhaler device. The additive material, which it will be appreciated is of a different material from the carrier particles, may be in the form of particles, the additive particles being attached to the surfaces of the carrier particles.

In International Specification WO 96/23485 many examples are given of additive materials which are such that the active particles are not liable to be released from the carrier particles before actuation of the inhaler device but are released during use of the inhaler device. "Actuation of the inhaler device" refers to the process during which a dose of the powder is removed from its rest position in the inhaler device, usually by a patient inhaling. That step takes place after the powder has been loaded into the inhaler device ready for use.

If it is desired to test whether or not the active particles of a powder are liable to be released from the carrier particles before actuation of the inhaler device a test can be carried out. A suitable test is described in International Specification WO96/23485 (Examples 12 and 13). A powder whose post-vibration homogeneity measured as a percentage coefficient of variation, after being subjected to the described test, is less than about 5% can be regarded as acceptable.

It is believed that additive material is attracted to and adheres to high energy sites on the surfaces of the carrier particles. On introduction of the active particles, many of the high energy sites are now occupied, and the active particles therefore occupy the lower energy sites on the surfaces of the carrier particles. That results in the easier and more efficient release of the active particles in the air stream created on inhalation, thereby giving increased deposition of the active particles in the lungs.

However, as indicated above, it has been found that the addition of more than a small amount of additive material can be disadvantageous because of the adverse effect on the ability to process the mix during commercial manufacture.

It is also advantageous for as little as possible of the additive material to reach the lungs on inhalation of the powder. Although the additive material will most advantageously be one that is safe to inhale into the lungs, it is still preferred that only a very small proportion, if any, of the additive material reaches the lung, in particular the lower lung. The considerations that apply when selecting the additive material and other features of the powder are therefore different from the considerations when a third component is added to carrier and active material for certain other reasons, for example to improve absorption of the active material in the lung, in which case it would of course be advantageous for as much as possible of the additive material in the powder to reach the lung.

The optimum amount of additive material will depend on the chemical composition and other properties of the additive material. In general, the amount of additive will be not more than 50% by weight, based on the total weight of the formulations. However, it is thought that for most additives the amount of additive material should be not more than 10%, more advantageously not more than 5%, preferably not more than 4% and for most materials will be not more than 2% or even not more than 1% by weight or not more than 0.25% based on the total weight of the formulation. In general, the amount of additive material is at least 0.01% by weight based on the total weight of the formulation.

Advantageously the additive material is an anti-adherent material and will tend to decrease the cohesion between the anti-adherent materials and the carrier particles. In order to determine whether a given material is an anti-adherent material, the test described in International Specification WO97/03649 (pages 6 and 7) using an "Aeroflow" apparatus may be used, anti-adherent materials being those additive materials that result in a lowering of the mean time between avalanches of the powder, as compared with the powder in the absence of the additive material.

Advantageously the additive material is an anti-friction agent (glidant) and will give better flow of powder in the dry powder inhaler which will lead to a better dose reproducibility from the inhaler device.

Where reference is made to an anti-adherent material, or to an anti-friction agent, the reference is to include those materials which will tend to decrease the cohesion between the active particles and the carrier particles, or which will tend to improve the flow of powder in the inhaler, even though they may not usually be referred to as anti-adherent material or an anti-friction agent. For example, leucine is an anti-adherent material as herein defined and is generally thought of as an anti-adherent material but lecithin is also an anti-adherent material as herein defined, even though it is not generally though of as being anti-adherent, because it will tend to decrease the cohesion between the active particles and the carrier particles. Advantageously, the additive material consists of physiologically acceptable material. As already indicated, it is preferable for only small amounts of additive material to reach the lower lung, and it is also highly preferable for the additive material to be a material which may be safely inhaled into the lower lung where it may be absorbed into the blood stream. That is especially important where the additive material is in the form of particles.

The additive material may include a combination of one or more materials.

It will be appreciated that the chemical composition of the additive material is of particular importance.

It will furthermore be appreciated that additive materials that are naturally occurring animal or plant substances will offer certain advantages.

Advantageously, the additive material includes one or more compounds selected from amino acids and derivatives thereof, and peptides and polypeptides having molecular weight from 0.25 to 100 Kda, and derivatives thereof. Amino acids, peptides or polypeptides and their derivatives are both physiologically acceptable and give acceptable release of the active particles on inhalation.

It is particularly advantageous for the additive material to comprise an amino acid. Amino acids have been found to give, when present in low amounts in a powder as additive material, high respirable fraction of the active materials with little segregation of the powder and also with very little of the amino acid being transported into the lower lung. In respect of leucine, a preferred amino acid, it is found that, for example, for an average dose of powder only about 10 μg of leucine would reach the lower lung. The additive material may comprise one or more of any of the following amino acids: leucine, isoleucine, lysine, valine, methionine, phenylalanine. The additive may be a salt of a derivative of an amino acid, for example aspartame or acesulfame K. Preferably, the additive particles consist substantially of leucine, advantageously L-leucine. As indicated above, leucine has been found to give particularly efficient release of the active particles on inhalation. Whilst the L-form of an amino acid is used in Examples described below, the D- and DL-forms may also be used.

Additive materials which comprise one or more water soluble substances offer certain advantages. This helps absorption of the substance by the body if the additive reaches the lower lung. The additive material may include dipolar ions, which may consist of zwitterions.

Alternatively, the additive material may comprise particles of a phospholipid or a derivative thereof. Lecithin has been found to be a good material for the additive material.

The additive material may include or consist of one or more surface active materials, in particular materials that are surface active in the solid state, which may be water soluble, for example lecithin, in particular soya lecithin, or substantially water insoluble, for example solid state fatty acids such as lauric acid, palmitic acid, stearic acid, erucic acid, behenic acid, or derivatives (such as esters and salts) thereof. Specific examples of such materials are: magnesium stearate; sodium stearyl fumarate; sodium stearyl lactylate; phospatidylcholines, phosphatidylglycerols and other examples of natural and synthetic lung surfactants; liposomal formulations; lauric acid and its salts, for example, sodium lauryl sulphate, magnesium lauryl sulphate; triglycerides such as Dynsan 118 and Cutina HR; and sugar esters in general.

Other possible additive materials include talc, titanium dioxide, aluminium dioxide, silicon dioxide and starch.

The expression "additive material" as used herein does not include crystalline sugars. Whereas small particles of one or more crystalline sugars may be present, and are indeed preferred to be present, as described below, formulations which contain small crystalline sugar particles will also contain a further substance which is an additive material in the sense in which that expression is used herein.

In the case of certain additive materials, it is important for the additive material to be added in a small amount. For example, magnesium stearate is highly surface active and should therefore be added in small amounts, for example, 2% by weight based on the weight of the formulation; phosphatidylcholines and phosphatidylglycerols on the other hand are less active and can usefully be added in greater amounts; in respect of leucine, which is still less active, an addition of 2% by weight leucine based on the weight of the powder gives good results in respect of the respirable fraction of the active particles, low segregation and low amount of leucine reaching the lower lung; it is explained in WO 96/23485 that an addition of a greater amount does not improve the results and in particular does not significantly improve the respirable fraction and therefore whilst even with 6% leucine a reasonable result is obtained that is not preferred since it results in an increased quantity of additive material being taken into the body and will adversely affect the processing properties of the mix. In the preferred formulations of the present invention using fissured carrier particles, however, it has been found that increased amounts of additive material may be used and give improved respirable fractions.

The additive material will often be added in particulate form but it may be added in liquid or solid form and for some materials, especially where it may not be easy to form particles of the material and/or where those particles should be especially small, it may be preferred to add the material in a liquid, for example as a suspension or a solution. Even then, however, the additive material of the finished powder may be in particulate form. An alternative possibility, however, that is within the scope of the invention is to use an additive material which remains liquid even in the final essentially particulate material which can still be described as a "dry powder".

In some cases improved clinical benefits will be obtained where the additive material is not in the form of particles of material. In particular, the additive material is less likely to leave the surface of the carrier particle and be transported into the lower lung.

Where the additive material of the finished powder is particulate, the nature of the particles may be significant. The additive particles may be non-spherical in shape. Advantageously, the additive particles are plate-like particles. Alternatively, the additive particles may be angular for example prisms, or dendritic in shape. Additive particles which are non-spherical may be easier to remove from the surfaces of the carrier particles than spherical, non-angular particles and plate-like particles may give improved surface interaction and glidant action between the carrier particles.

The surface area of the additive particles is also thought to be important. The surface area of the additive particles, as measured using gas absorption techniques, is preferably at least $5\,m^2g^{-1}$. In many cases it is found that additive material comprising small plate-like particles is preferred.

The additive may advantageously be magnesium stearate. Advantageously, the amount of magnesium stearate in the final formulation is comprised between at least 0.02 and not more than 2.5% by weight (which equates to 2.5 g per 100 g of final formulation). The amount of magnesium stearate may be between at least 0.05 and not more than 1.0% by weight, for example between 0.1 and not more than 0.6% by weight, or between 0.2 and 0.4% by weight. In some circumstances, in particular where the preferred fissured carrier particles are used, the amount of magnesium stearate may be preferred to be between 0.1 and 2% by weight, for example 0.5 to 1.7% by weight, especially 0.75 to 1.5% by weight. Advantageously the fraction with a fine particle size is composed of 90 to 99% by weight of the physiologically acceptable excipient and 1 to 10% by weight of the additive and the ratio between the fraction of fine particle size and the fraction of coarse carrier particle is comprised between 1:99 and 40:60% by weight, preferably between 5:95 and 30:70 percent by weight, even more preferably between 10:90 and 20:80% by weight.

The fine excipient particles of the mixture (i) in general constitute less than 40% by weight of the total formulation, and advantageously constitute no more than 20%, for example no more than 10%, of the total formulation weight. Preferably, the fine excipient particles constitute at least 4%, more preferably at least 5% of the total formulation weight.

In a preferred embodiment of the invention, the fraction with a fine particle size is composed of 98% by weight of a-lactose monohydrate and 2% by weight of magnesium stearate and the ratio between the fraction with a fine particle size and the coarse fraction made of a-lactose monohydrate particles is 10:90% by weight, respectively.

Advantageously the formulation of the invention has an apparent density before settling of at least 0.5 g/ml, preferably from 0.6 to 0.7 g/ml and a Carr index of less than 25, preferably less than 15.

In one of the embodiment of the invention, the excipient particles and additive particles are co-micronised by milling, advantageously in a ball mill, preferably until the final particle size of the mixture is less than 35 µm, preferably less than 30 µm, more preferably less than 15 µm. In some cases, co-micronisation for at least two hours may be found advantageous, although it will be appreciated that the time of treatment will generally be such that a desired size reduction is obtained. In a more preferred embodiment of the invention the particles are co-micronised by using a jet mill.

Alternatively, the mixture of the excipient particles with a starting particle size less than 35 μm, preferably less than 30 μm, more preferably less than 15 μm, with the additive particles will be prepared by mixing the components in a high-energy mixer for at least 30 minutes, preferably for at least one hour, more preferably for at least two hours.

In general, the person skilled in the art will select the most proper size of the fine excipient particles either by sieving, by using a classifier, or by suitably adjusting the time of co-milling.

The spheronisation step will be carried out by mixing the coarse carrier particles and the fine particle fraction in a suitable mixer, e.g. tumbler mixers such as Turbula, rotary mixers or instant mixer such as Diosna for at least 5 minutes, preferably for at least 30 minutes, more preferably for at least two hours, even more preferably for four hours. In a general way, the person skilled in the art will adjust the time of mixing and the speed of rotation of the mixer to obtain homogenous mixture.

When the formulation of the invention is prepared by co-mixing the coarse carrier particles, additive and the fine excipient particles all together, the process is advantageously carried out in a suitable mixer, preferably in a Turbula mixer for at least two hours, preferably for at least four hours.

The ratio between the spheronised carrier and the drug (the active ingredient) will depend on the type of inhaler device used and the required dose.

The mixture of the spheronised carrier with the active particles will be prepared by mixing the components in suitable mixers like those reported above.

Advantageously, at least 90% of the particles of the drug have a particle size less than 10 μm, preferably less than 6 μm.

The at least one active ingredient is preferably in the form of active particles. The active particles referred to throughout the specification will comprise an effective amount of at least one active agent that has therapeutic activity when delivered into the lung. The active particles advantageously consist essentially of one or more therapeutically active agents. Suitable therapeutically active agents may be drugs for therapeutic and/or prophylactic use. Active agents which may be included in the formulation include those products which are usually administered orally by inhalation for the treatment of disease such a respiratory disease, for example, β-agonists.

The active particles may comprise at least one β-agonist, for example one or more compounds selected from terbutaline, salbutamol, salmeterol and formoterol. If desired, the active particles may comprise more than one of those active agents, provided that they are compatible with one another under conditions of storage and use.

Preferably, the active particles are particles of salbutamol sulphate. References herein to any active agent are to be understood to include any physiologically acceptable derivative. In the case of the β-agonists mentioned above, physiologically acceptable derivatives include especially salts, including sulphates.

The active particles may be particles of ipatropium bromide.

The active particles may include a steroid, which may be, for example, fluticasone. The active principle may include a cromone which may be sodium cromoglycate or nedocromil. The active principle may include a leukotriene receptor antagonist.

The active particles may include a carbohydrate, for example heparin.

The active particles may advantageously comprise a therapeutically active agent for systemic use provided that that agent is capable of being absorbed into the circulatory system via the lungs. For example, the active particles may comprise peptides or polypeptides or proteins such as DNase, leukotrienes or insulin (including substituted insulins and pro-insulins), cyclosporin, interleukins, cytokines, anti-cytokines and cytokine receptors, vaccines (including influenza, measles, 'anti-narcotic' antibodies, meningitis), growth hormone, leuprolide and related analogues, interferons, desmopressin, immunoglobulins, erythropoeitin, calcitonin and parathyroid hormone. The formulation of the invention may in particular have application in the administration of insulin to diabetic patients, thus avoiding the normally invasive administration techniques used for that agent.

The powders of the invention may advantageously be for use in pain relief. Non-opioid analgesic agents that may be included as pain relief agents are, for example, alprazolam, amitriptyline, aspirin, baclofen, benzodiazepines, bisphosphonates, caffeine, calcitonin, calcium-regulating agents, carbamazepine, clonidine, corticosteroids, dantrolene, dexamethasone, disodium pamidronate, ergotamine, flecainide, hydroxyzine, hyoscine, ibuprofen, ketamine, lignocaine, lorazepam, methotrimeprazine, methylprednisolone, mexiletine, mianserin, midazolam, NSAIDs, nimodipine, octreotide, paracetamol, phenothiazines, prednisolone, somatostatin. Suitable opioid analgesic agents are: alfentanil hydrochloride, alphaprodine hydrochloride, anileridine, bezitramide, buprenorphine hydrochloride, butorphanol tartrate, carfentanil citrate, ciramadol, codeine, dextromoramide, dextropropoxyphene, dezocine, diamorphine hydrochloride, dihydrocodeine, dipipanone hydrochloride, enadoline, eptazocine hydrobromide, ethoheptazine citrate, ethylmorphine hydrochloride, etorphine hydrochloride, fentanyl citrate, hydrocodone, hydromorphone hydrochloride, ketobemidone, levomethadone hydrochloride, levomethadyl acetate, levorphanol tartrate, meptazinol hydrochloride, methadone hydrochloride, morphine, nalbuphine hydrochloride, nicomorphine hydrochloride, opium, hydrochlorides of mixed opium alkaloids, papaveretum, oxycodone, oxymorphone hydrochloride, pentamorphone, pentazocine, pethidine hydrochloride, phenazocine hydrobromide, phenoperidine hydrochloride, picenadol hydrochloride, piritramide, propiram furmarate, remifentanil hydrochloride, spiradoline mesylate, sufentanil citrate, tilidate hydrochloride, tonazocine mesylate, tramadol hydrochloride, trefentanil.

The technique could also be used for the local administration of other agents for example for anti cancer activity, anti-virals, antibiotics, muscle relaxants, antidepressants, antiepileptics or the local delivery of vaccines to the respiratory tract.

In one form of the invention, the active ingredient is not an active ingredient selected from the group consisting of budeponide and its epimers, formoterol, TA2005 and its stereoisomers, salts thereof and combinations thereof.

The active particles advantageously have a mass median aerodynamic diameter in the range of up to 15 μm, for example from 0.01 to 15 μm, preferably from 0.1 to 10 μm, for example from 1 to 8 μm. Most preferably, the mass median aerodynamic diameter of the active particles is not exceeding 5 μm. The active particles are present in an effective amount, for example, at least 0.01% by weight, and may be present in an amount of up to 90% by weight based on the total weight of carrier particles, additive materials and active particles. Advantageously, the active particles are present in an amount not exceeding 60% by weight based on the total weight of carrier particles, additive particles and active particles.

It will be appreciated that the proportion of active agent present will be chosen according to the nature of the active agent. In many cases, it will be preferred for the active agent to constitute no more than 10%, more preferably no more than 5%, and especially no more than 2% by weight based on the total weight of carrier particles, additive particles and active particles.

The process of the invention is illustrated by the following examples.

EXAMPLE 1

Hard-Pellet Formulation Containing Coarse Lactose (CapsuLac 212-355 μm), a Micronized Pre-Blend Lactose/Magnesium Stearate Mixture Obtained by Jet Milling and Formoterol Fumarate as Active Ingredient a) Preparation of the formulation α-Lactose monohydrate SpheroLac 100 (Meggle EP D30) with a starting particle size of 50 to 400 μm (d(v, 0.5) of about 170 μm) and magnesium stearate with a starting particle size of 3 to 35 μm (d(v, 0.5) of about 10 μm) in the ratio 98:2% by weight were co-milled in a jet mill apparatus. At the end of the treatment, a significant reduction of the particle size was observed (blend A).

85% by weight of α-lactose monohydrate CapsuLac (212-355 μm) was placed in a 240 ml stainless steel container, then 15% by weight of blend A was added. The blend was mixed in a Turbula mixer for 2 hours at 42 rpm (blend B).

Micronised formoterol fumarate was added to the blend B and mixed in a Turbula mixer for 10 mins at 42 rpm to obtain a ratio of 12 μg of active to 20 mg of carrier; the amount of magnesium stearate in the final formulation is 0.3% by weight. The final formulation (hard pellet formulation) was left to stand for 10 mins then transferred to amber glass jar.

b) Characterisation of the micronised mixture (blend A) The micronized mixture (blend A) was characterised by particle size analysis (Malvern analysis), water contact angle and degree of molecular surface coating calculated according to Cassie et al. in Transaction of the Faraday Society 40; 546,1944.

The results obtained are reported in Table 1.

TABLE 1

| Micronised mixture (blend A) | |
|---|---|
| Particle size distribution (μm) | Malvern |
| d (v, 0.1) | 1.58 |
| d (v, 0.5) | 4.19 |
| d (v, 0.9) | 9.64 |
| Water contact angle | 40° |
| Degree of coating | 15% * |

* α-Lactose monohydrate water contact angle 12°; magnesium stearate water contact angle 118°.

c) Chemical and technological characterisation of the hard-pellet formulation.

The formulation mixture was characterised by its density/flowability parameters and uniformity of distribution of the active ingredient.

The apparent volume and apparent density were tested according to the method described in the European Pharmacopoeia (Eur. Ph.).

Powder mixtures (100 g) were poured into a glass graduated cylinder and the unsettled apparent volume $V_0$ is read; the apparent density before settling (dv) was calculated dividing the weight of the sample by the volume $V_0$. After 1250 taps with the described apparatus, the apparent volume after settling ($V_{1250}$) is read and the apparent density after settling (ds) was calculated.

The flowability properties were tested according to the method described in the Eur. Ph.

Powder mixtures (about 110 g) were poured into a dry funnel equipped with an orifice of suitable diameter that is blocked by suitable mean. The bottom opening of the funnel is unblocked and the time needed for the entire sample to flow out of the funnel recorded. The flowability is expressed in seconds and tenths of seconds related to 100 g of sample.

The flowability was also evaluated from the Carr's index calculated according to the following formula:

$$\text{Carr's index } (\%) = \frac{ds - dv}{ds} \times 100$$

A Carr index of less than 25 is usually considered indicative of good flowability characteristics.

The uniformity of distribution of the active ingredient was evaluated by withdrawing 10 samples, each equivalent to about a single dose, from different parts of the blend. The amount of active ingredient of each sample was determined by High-Performance Liquid Chromatography (HPLC).

The results are reported in Table 2.

TABLE 2

| Chemical and Technological Parameters of the hard pellet formulation | |
|---|---|
| Apparent volume/density | |
| App. volume ($V_0$) before settling | 156 ml |
| App. density ($d_v$) before settling | 0.64 g/ml |
| App. volume ($V_{1250}$) after settling | 138 ml |
| App. density ($d_9$) after settling | 0.73 g/ml |
| Flowability | |
| Flow rate through 4 mm Ø | 152 8/100 g |
| Carr Index | 12 |
| Uniformity of distribution of active ingredient | |
| Mean value | 12.1 μg |
| RSD | 2.2% | d) Determination of the aerosol performances.

An amount of powder for inhalation was loaded in a multidose dry powder inhaler (Pulvinal®—Chiesi Pharmaceutical SpA, Italy).

The evaluation of the aerosol performances was performed by using a modified Twin Stage Impinger apparatus, TSI (Apparatus of type A for the aerodynamic evaluation of fine particles described in FU IX, 4° supplement 1996). The equipment consists of two different glass elements, mutually connected to form two chambers capable of separating the powder for inhalation depending on its aerodynamic size; the chambers are referred to as higher (stage 1) and lower (stage 2) separation chambers, respectively. A rubber adaptor secures the connection with the inhaler containing the powder. The apparatus is connected to a vacuum pump which produces an air flow through the separation chambers and the connected inhaler. Upon actuation of the pump, the air flow carries the particles of the powder mixture, causing them to deposit in the two chambers depending on their aerodynamic diameter. The apparatus used were modified in the Stage 1 Jet in order to obtained an aerodynamic diameter limit value, dae, of 5 μm at an air flow of 30 l/min, that is considered the relevant flow rate for Pulvinal® device. Particles with higher dae deposit in Stage 1 and particles with lower dae in Stage 2. In both stages, a minimum volume of solvent is used (30 ml in Stage 2 and 7 ml in Stage 1) to prevent particles from adhering to the walls of the apparatus and to promote the recovery thereof.

The determination of the aerosol performances of the mixture obtained according to the preparation process a) was carried out with the TSI applying an air flow rate of 30 l/min for 8 seconds.

After nebulization of 10 doses, the Twin Stage Impinger was disassembled and the amounts of drug deposited in the two separation chambers were recovered by washing with a solvent mixture, then diluted to a volume of 100 and 50 ml in two volumetric flasks, one for Stage 1 and one for Stage 2, respectively. The amounts of active ingredient collected in the two volumetric flasks were then determined by High-Performance Liquid Chromatography (HPLC). The following parameters, were calculated: i) the shot weight as mean expressed as mean and relative standard deviation (RSD) ii) the fine particle dose (FPD) which is the amount of drug found in stage 2 of TSI; iii) the emitted dose which is the amount of drug delivered from the device recovered in stage 1+stage 2; iv) the fine particle fraction (FPF) which is the percentage of the emitted dose reaching the stage 2 of TSI.

The results in terms of aerosol performances are reported in Table 3.

TABLE 3

| Aerosol performances | | | |
|---|---|---|---|
| Shot weight mg (%) | Emitted dose μg | FPD μg | FPF % |
| 20.0 (7.8) | 9.40 | 4.44 | 47.2 |

The formulation of the invention shows very good flow properties as demonstrated by the Carr index; this parameter is very important to obtain consistency of the delivered dose when a multi-dose dry powder inhalers with powder reservoir is used. The aerosol performance of the formulation is very good as well with about 50% of the drug reaching the stage 2 of the TSI.

EXAMPLE 2

Hard-Pellet Formulation Containing Coarse Lactose (CapsuLac 212-355 μm), a Micronized Pre-Blend Lactose/Magnesium Stearate Mixture Obtained by Ball Milling and Formoterol Fumarate as Active Ingredient Blend A was prepared as described in the Example 1 but using α-lactose monohydrate SorboLac 400 with a starting particle size below 30 μm (d(v, 0.5) of about 10 μm) and carrying out the co-micronisation in a ball milling apparatus for 2 hours.
Blend B was prepared according to the Example 1 but after mixing for 6 mins and then screening through a 355 μm sieve.

The hard pellet final formulation was prepared according to the Example 1.

The particle size distribution, the water contact angle and the degree of coating for the micronized mixture (blend A), and the uniformity of distribution of the active ingredient for the final formulation (blend B), determined as previously described, are reported in Table 4.

Analogous results were achieved after preparing blend B by mixing for 4 hours without screening through a sieve.

TABLE 4

| Characterisation of blends A and B | |
|---|---|
| Micronised mixture (blend A) | |
| Particle size distribution | |
| (μm) Malvern | |
| d (v, 0.1) | 0.72 μm |
| d (v, 0.5) | 2.69 μm |
| d (v, 0.9) | 21.98 μm |
| water contact angle | 52° |
| degree of coating | 25% |
| Final formulation (blend B) | |
| Uniformity of distribution | ean = 11.84 μg |
| of the active ingredient | SD = 1.83% |

The in-vitro performances, determined as previously described, are reported in Table 5.

TABLE 5

| Aerosol performances | | | |
|---|---|---|---|
| Shot weight mg (%) | Emitted dose μg | FPD μg | FPF % |
| 20.8 (6.9) | 8.57 | 4.28 | 49.9 |

As it can be appreciated from the results, also such formulation show excellent characteristics either in terms of flowability properties and in terms of aerosol performances.

EXAMPLE 3

Determination of the Suitable Amount of Magnesium Stearate to be Added in the Formulation Samples of pre-blends were prepared as described in Example 2 in a ball milling apparatus for 2 hours using α-Lactose monohydrate SorboLac 400 (Meggle microtose) with a starting particle size below 30 μm (d(v, 0.5) of about 10 μm) and magnesium stearate with a starting particle size of 3 to 35 μm (d(v, 0.5) of about 10 μm) in the ratio 98:2, 95:5 and 90:10% by weight (blends A). Blends B and the hard pellet final formulation were prepared as previously described; the amount of magnesium stearate in the final formulations turns out to be 0.3, 0.75 and 1.5% by weight, respectively. The uniformity of distribution of active ingredient and the in-vitro aerosol performance were determined as previously described.

The results obtained are reported in Table 6.

TABLE 6

Uniformity of distribution and in-vitro aerosol performances

|  | Mg stearate 0.3% | Mg etearate 0.75% | Mg etearate 1.5% |
|---|---|---|---|
| Content uniformity |  |  |  |
| Mean (μg) | 11.84 | — | — |
| RSD (%) | 1.83 | — | — |
| Shot weight |  |  |  |
| Mean (μg) | 20.8 | 24.7 | 23.0 |
|  | 4.28 |  |  |
|  | 49.9 |  |  |
| RSD (%) | 6.9 | 6.5 | 2.4 |
| Emitted dose (μg) | 8.57 | 10.1 | 11.1 |
| FPD (μg) | 4.28 | 3.5 | 3.6 |
| FPF (%) | 49.9 | 35 | 32 |

In all cases, good performances in terms of fine particle dose are obtained, in particular with 0.3% by weight of magnesium stearate in the final formulation.

EXAMPLES 4

Ordered Mixtures Powder Formulations

Powders mixtures were prepared by mixing of commercially available α-lactose monohydrate with different particle size and formoterol fumarate to obtain a ratio of 121.1 g of active to 20 mg of carrier. Blending was carried out in glass mortar for 30 mins. The uniformity of distribution of active ingredient and the in-vitro aerosol performances were determined as previously described. The results are reported in Table 7.

TABLE 7

Uniformity of distribution and in-vitro aerosol performances

|  | Spherolac 100 (63-90 μm) | Spherolac 100 (90-150 μm) | Spherolac 100 (150-250 μm) | Pharmatose 325M (30-100 μm) |
|---|---|---|---|---|
| Content uniformity |  |  |  |  |
| Mean (μg) | 11.89 | 11.81 | 12.98 | 11.90 |
| RSD (%) | 3.88 | 2.17 | 9.03 | 10.10 |
| Shot weight |  |  |  |  |
| Mean (μg) | 25.28 | 25.23 | 22.02 | 22.40 |
| RSD (%) | 7.73 | 3.39 | 6.93 | 22.00 |
| Emitted Dose (μg) | 11.10 | 10.30 | 8.50 | 7.80 |
| FPD (μg) | 1.40 | 0.70 | 0.60 | 1.20 |
| FPF (%) | 12.6 | 6.8 | 7.1 | 15.4 |

The results indicate that, upon preparation of ordered mixtures containing formoterol fumarate as active ingredient according to the teaching of the prior art, the performance of the formulations are very poor.

EXAMPLE 5

Powder Formulations Containing Different Amounts of Fine Lactose Particles

Carrier A—α-Lactose monohydrate Spherolac 100 (90-150 μm) and Sorbolac 400 with a particle size below 30 μm (d(v, 0.5) of about 10 μm) in the ratio 95:5 percent by weight were mixed in a mortar for 15 mins.

Carrier B—α-Lactose monohydrate Spherolac 100 (90-150 μm) and micronised lactose (particle size below 5 μm) in the ratio 95:5 w/w were mixed in a mortar for 15 mins.

Carrier C—α-Lactose monohydrate Spherolac 100 (150-250 μm) and Sorbolac 400 with a particle size below 30 μm (d(v, 0.5) of about 10 μm) in the ratio 95:5% by weight were mixed in a mortar for 30 mins.

Carrier D—α-Lactose monohydrate Spherolac 100 (150-250 μm) and Sorbolac 400 particle size below 30 μm (d(v, 0.5) of about 10 μm) in the ratio 90:10% by weight were mixed in a mortar for 30 mins.

In the case of all the formulations tested, the carriers were mixed with formoterol fumarate in mortar for 15 mins to obtain a ratio of 12 μm of active to 25 mg of carrier.

The results in terms of content uniformity and in-vitro aerosol performances are reported in Table 8.

TABLE 8

Content uniformity and in-vitro aerosol performances

|  | Carrier A | Carrier B | Carrier C | Carrier D |
|---|---|---|---|---|
| Content uniformity |  |  |  |  |
| Mean (μg) | 10.96 | 10.50 | 11.86 | — |
| RSD (%) | 1.80 | 15.01 | 7.10 | 0 |

TABLE 8-continued

Content uniformity and in-vitro aerosol performances

|  | Carrier A | Carrier B | Carrier C | Carrier D |
|---|---|---|---|---|
| Shot weight |  |  |  |  |
| Mean (μg) | 23.46 | 25.29 | 25.7 | 19.53 |
| RSD (%) | 51.43 | 4.19 | 3.77 | 32.02 |

TABLE 8-continued

Content uniformity and in-vitro aerosol performances

|  | Carrier A | Carrier B | Carrier C | Carrier D |
|---|---|---|---|---|
| Emitted Dose (μg) | 10.40 | 9.5 | 10.1 | 5.92 |
| FPD (μg) | 1.60 | 2.3 | 2.3 | 1.30 |
| FPF(%) | 15.8 | 24.4 | 22.68 | 21.6 |

The results indicate that the performance of such formulations under the test conditions are very poor.

EXAMPLE 6

Hard-Pellet Formulation Containing Coarse Lactose (PrismaLac 40 Fraction Below 3551 m) and Fine Lactose α-Lactose monohydrate PrismaLac 40 with a particle size below 355 μm and Sorbolac 400 with a particle size below 30 μm (d(v, 0.5) of about 10 μm) in the ratio 60:40% by weight were first manually agitated for 10 mins to promote aggregation and then blended in a Turbula mixer for 30 mins at 42 rpm. The spheronised particles were mixed with formoterol fumarate in a Turbula mixer for 30 mins at 42 rpm to obtain a ratio of 12 μg of active to 15 μg of carrier.

The results in terms of uniformity of distribution of active ingredient and in-vitro aerosol performances are reported in Table 9.

TABLE 9

Uniformity of distribution of active ingredient and in-vitro aerosol performances

|  | Spheronised particles |
|---|---|
| Content uniformity |  |
| Mean (μg) | 11.90 |
| RSD (%) | 18.46 |
| Shot weight |  |
| Mean (μg) | 18.10 |
| RSD (%) | 6.80 |
| Emitted Dose (μg) | 11.10 |
| FPD (μg) | 2.10 |
| FPF(%) | 18.9 |

The formulation without magnesium stearate thus has poor performance under the test conditions.

EXAMPLE 7

Effect of the Addition of Magnesium Stearate by Simple Mixing

Formulation A—α-Lactose monohydrate Pharmatose 325M (30-100 μm) and magnesium stearate in the ratio 99.75:0.25% by weight were blended in a Turbula mixer for 2 hours at 42 rpm. The blend was mixed with formoterol fumarate in a Turbula mixer for 30 mins at 42 rpm to obtain a ratio of 12 μg of active to 25 mg of carrier.
Formulation B—as reported above but α-Lactose monohydrate SpheroLac 100 (90-150 μm) instead of Pharmatose 325M.
Formulation C—α-Lactose monohydrate PrismaLac 40 (with a particle size below 355 μm) and micronised lactose with a particle size below 5 μm in the ratio 40:60% by weight were mixed in a Turbula mixer for 60 mins at 42 rpm 99.75% by weight of the resulting blend and 0.25% by weight of magnesium stearate were mixed in a Turbula mixer for 60 mins at 42 rpm. The resulting blend was finally mixed with formoterol fumarate in a Turbula mixer for 30 mins at 42 rpm to obtain a ratio of 12 μg of active to 15 mg of carrier.

Formulation D—Sorbolac 400 with a particle size below 30 μm (d(v, 0.5) of about 10 μm) and magnesium stearate in the ratio 98:2% by weight were mixed in a high shear mixer for 120 mins (blend A). 85% by weight a-lactose monohydrate CapsuLac (212-355 μm) and 15% by weight of blend A were mixed in Turbula for 2 hours at 42 rpm (blend B); the amount of magnesium stearate in the final formulation is 0.3% by weight. Micronised formoterol fumarate was placed on the top of blend B and mixed in a Turbula mixer for 10 mins at 42 rpm to obtain a ratio of 12 μg of active to 20 mg of carrier.

Formulation E—Micronized lactose with a particle size below 10 μm (d(v, 0.5) of about 3 μm) and magnesium stearate in the ratio 98:2% by weight were mixed in a Sigma Blade mixer for 60 mins (blend A). 85% by weight of a-lactose monohydrate CapsuLac (212-355 μm) and 15% by weight of blend A were mixed in Turbula for 2 hours at 42 rpm (blend B); the amount of magnesium stearate in the final formulation is 0.3% by weight. Micronised formoterol fumarate was placed on the top of blend B and mixed in a Turbula mixer for 10 mins at 42 rpm to obtain a ratio of 12 μg of active to 20 mg of carrier.

The results in terms of uniformity of distribution of active ingredient and in-vitro aerosol performances are reported in Table 10.

TABLE 10

Uniformity of distribution of active ingredient and in-vitro aerosol performances

|  | Formulations A | Formulations B | Formulations C | Formulations D | Formulations E |
|---|---|---|---|---|---|
| Content uniformity |  |  |  |  |  |
| Mean (μg) | 7.96 | 10.50 | 9.10 | 10.68 | 11.32 |
| RSD (%) | 2.16 | 8.30 | 24.90 | 2.80 | 3.0 |
| Shot weight |  |  |  |  |  |
| Mean (μg) | 24.10 | 26.50 | 12.50 | 22.07 | 21.87 |
| RSD (%) | 34.60 | 8.20 | 15.30 | 2.50 | 4.0 |
| Emitted Dose (μg) | 6.10 | 7.60 | 9.60 | 8.60 | 9.93 |
| FPD (μg) | 0.60 | 0.90 | 1.60 | 3.38 | 4.80 |
| FPF(%) | 9.8 | 11.8 | 16.7 | 39.3 | 48.37 |

The formulations where magnesium stearate is added, by simple mixing, to the lactose (formulations A-B) and without the presence of added fine excipient show very poor performance.

Formulations where magnesium stearate is added by a high energy mixing to a small amount of fine lactose (blend A of the formulations D and E) show a significant increase in performance. In addition, the particle size of the fine lactose used has a significant effect on the deaggregation properties of the final formulation; in fact, formulation E prepared using a micronized lactose shows a significant improved performance compared with formulation D.

EXAMPLE 8

Effect of the Amount of Micronized Pre-Blend in the Final Formulation

α-Lactose monohydrate SpheroLac 100 (Meggle EP D30) with a starting particle size of 50 to 400 μm (d(v, 0.5) of about 170 μm and magnesium stearate with a starting particle size of 3 to 35 μm (d(v, 0.5) of about 10 μm) in the ratio 98:2% by weight were co-milled in a jet mill apparatus (blend A) Different ratios of α-lactose monohydrate Capsulac (212-355 μm) and blend A were placed in a stainless steel container and mixed in a Turbula mixer for four hours at 32 rpm (blends B)

Micronised formoterol fumarate was placed on the top of blends B and mixed in a Turbula mixer for 30 mins at 32 rpm to obtain a ratio of 12 μg of active to 20 mg total mixture. The amount of magnesium stearate in the final formulation ranges between 0.05 and 0.6% by weight.

The results in terms of uniformity of distribution of active ingredient and in-vitro aerosol performances are reported in Table 11.

TABLE 11

Uniformity of distribution of active ingredient and in-vivo aerosol performance

|  | Ratio 97.5:2.5 | Ratio 95:5 | Ratio 92.5:7.5 | Ratio 90:10 | Ratio 80:20 | Ratio 70:30 |
|---|---|---|---|---|---|---|
| Content uniformity |  |  |  |  |  |  |
| Mean (μg) | 11.29 | 12.25 | 11.53 | 11.93 | 11.96 | 12.00 |
| RSD (%) | 3.8 | 5.7 | 1.5 | 2.5 | 2.0 | 2.0 |
| Shot weight |  |  |  |  |  |  |
| Mean (μg) | 19.27 | 20.26 | 20.38 | 21.05 | 22.39 | 22.48 |
| RSD (%) | 4.7 | 3.3 | 3.2 | 4.3 | 3.5 | 3.7 |
| Emitted Dose (μg) | 10.58 | 9.20 | 10.65 | 9.18 | 9.63 | 9.88 |
| FPD (μg) | 4.18 | 5.10 | 6.78 | 5.9 | 5.33 | 5.28 |
| FPF(%) | 39.4 | 55.4 | 63.6 | 64.3 | 55.3 | 53.4 |

The results indicate that the performances of all the formulations are good.

EXAMPLE 9

Formulation Containing Lactose 90-150 μm, a Micronized Pre-Blend Lactose/Magnesium Stearate Mixture Obtained by Jet Milling and Formoterol as Active Ingredient α-Lactose monohydrate SpheroLac 100 (Meggle EP D30) with a starting particle size of 50 to 400 μm (d(v, 0.5) of about 170 μm and magnesium stearate with a starting particle size of 3 to 35 μm (d(v, 0.5) of about 10 μm) in the ratio 98:2% by weight were co-milled in a jet mill apparatus (blend A).

92.5% by weight of α-lactose monohydrate Spherolac with a starting particle size of 90 to 150 μm (d(v, 0.5 of about 145 μm) and 7.5% by weight of blend A were placed in a stainless steel container and mixed in a Turbula mixer for four hours at 32 rpm (blends B)

Micronised formoterol fumarate was placed on the top of blends B and mixed in a Turbula mixer for 30 mins at 32 rpm to obtain a ratio of 12 μg of active to 20 mg total mixture. The amount of magnesium stearate in the final formulation is 0.15% by weight.

The results in terms of uniformity of distribution of active ingredient and in-vitro aerosol performances are reported in Table 12.

TABLE 12

Uniformity of distribution of active ingredient and in-vitro aerosol performances

| Content uniformity |  |
|---|---|
| Mean (μg) | 11.75 |
| RSD (%) | 1.50 |
| Shot weight |  |
| Mean (μg) | — |
| RSD (%) | — |
| Emitted Dose (μg) | — |
| FPD (μg) | 5.71 |
| FPF(%) | 45.2 |

From the reported results, it can be appreciated that, as long as the fraction of fine particles is less than 10% by weight, the performances of a formulation containing standard lactose as coarse carrier fraction and a fine particle fraction excipient obtained either by co-milling or by co-mixing, are very good.

EXAMPLE 10

Effect of the Time of Mixing

Different blends were prepared by co-mixing CapsuLac 212-355 μm, micronized lactose with a particle size below 10 μm (d(v, 0.5) of about 3 μm) and magnesium stearate in the ratio 89.8:10:0.2% by weight, in a Turbula mixer (32 rpm) at increasing mixing time (1, 2 and 4 hours).

Micronised formoterol fumarate was placed on the top of each blend and mixed in a Turbula mixer for 30 mins at 32 rpm to obtain a ratio of 12 μg of active to 20 mg total mixture.

The results in terms of fine particle fraction (FPF) are reported in Table 13.

TABLE 13

Effect of the mixing time on FPF

| Time of mixing | Fine particle fraction (%) |
|---|---|
| 1 hour | 21.0 |
| 2 hours | 34.2 |
| 4 hours | 40.5 |

The results indicate that good performances in terms of fine particle fraction are achieved after mixing for at least two hours.

EXAMPLE 11

20 g of Microfine lactose (Burculo—MMAD about 8 μm) and 0.4 g of L-leucine (Ajinomoto) were combined and placed in a stainless steel ball mill, filled with stainless steel balls of varying diameter to approximately 50% of the mill volume. The mill was rotated at approximately 60 RPM for about 120 minutes. The milled material (MMAD about 5 μm) was then recovered from the mill and from the surface of the balls, and is referred to below as the fines.

8 g of sieved Prismalac lactose was weighed into a glass vessel. Prismalac (trade mark) lactose is sold in the UK by Meggle for use in tablet manufacture. The lactose, as purchased, had been sieved on a stack of sieves in order to recover the sieve fraction passing through a 600 µm mesh sieve, but not passing through a 355 µm mesh sieve. That fraction is referred to below as 355-600 Prismalac and has a mean tapped density of 0.49 g/cm$^3$ and a bulk density as measured by mercury intrusion porosimetry of 0.47 g/cm$^3$.

1 g of the fines obtained as described above, and 1 g of micronised salbutamol sulphate (MMAD-2 µm) was added to the 355-600 Prismalac in the glass vessel. The glass vessel was sealed and the vessel located in a "Turbula" tumbling blender. The vessel and contents were tumbled for approximately 30 minutes at a speed of 42 RPM.

The formulation so obtained was loaded into size 3 gelatin capsules at 20 mg per capsule. The loaded capsules were rested for a period of 24 hours. Three capsules were then fired sequentially into a Twin Stage Impinger at a flow rate of 60 liters per minutes, with a modified stage 1 jet of 12.5 mm internal diameter, which was estimated to produce a cut-off diameter of 5.4 μm. The operation of the Twin Stage Impinger is described in WO95/11666. Modification of a conventional Twin Stage Impinger, including the use of modified stage 1 jets, is described by Halworth and Westmoreland (J. Pharm. Pharmacol. 1987, 39:966-972).

TABLE 14

| | Example 1 | | Comparison 1 | Comparison 2 |
|---|---|---|---|---|
| 355-600 Prismalac lactose | 8 g | 80% | 8 g | 4 g |
| Salbutamol sulphate | 1 g | 10% | 1 g | 0.5 g |
| Microfine lactose | 0.9804 g | 9.804% | — | 0.5 g |
| Leucine | 0.0196 g | 0.196% | | — |
| Fine particle fraction | 50% | | 10% | 40% |

The composition of the formulation is summarised in Table 14 above.

As shown in Table 14, the fine particle fraction is improved in the presence of added fine lactose (Comparison 2) as compared with a formulation which contains no added fine lactose (Comparison 1). The best performance is obtained from the formulation according to the invention, containing leucine as well as fine lactose. On omission of the Prismalac from the ingredients of Example 11, the formulation was found to have very poor flow properties, preventing reliable and reproducible metering. As a result, the fine particle fraction was found to be very variable.

EXAMPLE 12

Example 11 was repeated using Prismalac lactose which had been sieved, the sieve fractions of 212 to 355 μm (with mean tapped density 0.65 g/cm$^3$ and a bulk density as measured by mercury intrusion porosimetry of 0.57 g/cm$^3$) being recovered and used instead of the 355-600 Prismalac lactose used in Example 11. Once again, a fine particle fraction of about 50% was obtained.

EXAMPLE 13

Example 11 was repeated replacing the leucine by one of the following: lecithin, stearylamine, magnesium stearate, and sodium stearyl fumarate.

The results are summarised in Table 15.

TABLE 15

| Additive | Fine particle fraction |
|---|---|
| Lecithin | 50% |
| Stearylamine | 50% |
| Purified phosphatidyl cholines | 35% |
| Sodium stearyl fumarate | 40% |

EXAMPLE 14

95 g of Microfine lactose (Borculo) was placed in a ceramic milling vessel (manufactured by the Pascall Engineering Company). 5 g of additive material (L-leucine) and the ceramic milling balls were added. The ball mill was tumbled at 60 rpm for 5 hours. The powder was recovered by sieving to remove the milling balls.

0.9 g of the composite excipient particles so obtained containing 5% 1-leucine in Microfine lactose was blended with 0.6 g of budesonide by hand in a mortar. This blending could also be performed, for example, in a high shear blender, or in a ball mill or in a centrifugal mill. 20 parts by weight sample of this powder were blended with 80 parts by weight of a coarse carrier lactose (sieve-fractionated Prismalac—355 to 600 μm fraction) by tumbling. The powder was fired from a Cyclohaler at a flow rate of 60 l/minute in a multi-stage liquid impinger. The fine particle fraction (<approx. 5 μm) was 45%.

EXAMPLE 15

98 g of Microfine (MMAD approximately 8 μm) lactose (manufactured by Borculo) was placed in a stainless steel milling vessel. 300 g of stainless steel milling balls varying from 10 to 3 mm diameter were added. 2 g of lecithin was added and the vessel was located in a Retsch S100 Centrifugal Mill. The powder was milled for 30 minutes at 580 rpm and was then sieved to remove the milling balls.

1 g of salbutamol sulphate was added to 1 g of the composite excipient particles so obtained containing 2% lecithin, and to 8 g of sieve-fractionated Prismalac lactose (355 to 600 μm fraction). The mixture was tumbled for 30 minutes at 42 rpm. The resulting powder was fired from a Cyclohaler at a flow rate of 60 liters per minute into a twin-stage impinger, giving a fine particle fraction (<approx. 5 microns) of about 44%. A similar example with a 2% leucine precursor gave a fine particle fraction (<approx. 5 μm) of 52%.

Other additive materials that may be used instead of lecithin to form composite excipient particles as described above are: magnesium stearate, calcium stearate, sodium stearate, lithium stearate, stearic acid, stearylamine, soya lecithin, sodium stearyl fumarate, 1-leucine, 1-isoleucine, oleic acid, starch, diphosphatidyl choline, behenic acid, glyceryl behenate, and sodium benzoate. Pharmaceutically acceptable fatty acids and derivatives, waxes and oils may also be used.

EXAMPLE 16

10 g of Microfine lactose (Borculo) was combined with 1 g of magnesium stearate and 10 cm$^3$ cyclohexane. 50 g of 5 mm balls were added and the mixture was milled for 90 minutes. The powder was recovered by leaving the paste in a fume hood overnight to evaporate the cyclohexane and then ball milling for 1 minute.

0.5 g of salbutamol sulphate was added to 0.5 g of the composite excipient particles so obtained containing magnesium stearate, and to 4 g of sieve-fractionated Prismalac lactose (355-600 µm fraction). This was tumbled for 30 minutes at 62 rpm. The resulting powder was fired from a Cyclohaler at a flow rate of 60 liters per minute into a twin-stage impinger, giving a fine particle fraction (<approx. 5 µm) of 57%. The experiment was repeated using composite excipient particles containing 20% magnesium stearate and similar results were obtained.

EXAMPLE 17

10 g of Microfine lactose (Borculo) was combined with 1 g of leucine and 10 cm$^3$ cyclohexane. 50 g of 5 mm balls were added and the mixture was milled for 90 minutes. The powder was recovered by leaving the paste in a fume hood overnight to evaporate the cyclohexane and then ball milling for 1 minute.

0.5 g of salbutamol sulphate, 0.25 g of composite excipient particles made as described in Example 16 containing magnesium stearate, 0.25 g of composite excipient particles made as described above containing leucine, and 4 g of sieve-fractionated Prismalac (355-600 µm fraction) were all combined. The mixture was tumbled for 30 minutes at 62 rpm. The resulting powder was fired from a Cyclohaler at a flow rate of 60 liters per minute into a twin-stage impinger, giving a fine particle fraction (<approx. 5 µm) of ~65%.

EXAMPLE 18

10 g of Microfine lactose (Borculo) was combined with 1 g of lecithin and 10 cm$^3$ cyclohexane. 50 g of 5 mm balls were added and the mixture was milled for 90 minutes. The powder was recovered by leaving the paste in a fume hood overnight to evaporate the cyclohexane and then ball milling for 1 minute.

0.5 g of salbutamol sulphate was added to 0.25 g of the composite excipient particles so obtained containing lecithin, 0.25 g of composite excipient particles made as described in Example 17 containing leucine, and 4 g of sieve-fractionated Prismalac lactose (355-600 µm fraction). The mixture was tumbled for 30 minutes at 62 rpm. The resulting powder was fired from a Cyclohaler at a flow rate of 60 liters per minute into a Twin-Stage Impinger, giving a fine particle fraction (<approx. 5 µm) of 68%.

EXAMPLE 19

95 g Sorbolac 400 (Meggle) were combined with 5 g of magnesium stearate and 50 ml dichloromethane and milled in a Retsch 5100 centrifugal mill with 620 g of 5 mm stainless steel balls in a stainless steel vessel for 90 minutes at 500 rpm. The powder was recovered after evaporation of the dichloromethane by briefly milling (1 minute) and subsequent sieving. 10 g of the composite excipient/additive particles so obtained were added to 89.5 g of sieve fractionated Prismalac lactose (355-600 µm fraction). The mixture was tumbled for 30 minutes at 60 rpm, then 0.5 g budesonide was added and tumbling continued for a further 30 minutes at 60 rpm. The powder was fired from a Cyclohaler at 60 l/minute into a Twin-Stage Impinger, and gave a fine particle fraction (<5 approx. µm) of about 80%.

EXAMPLE 20

(a) A pre-blend was made by milling an additive material and microfine lactose (<20 micron) together in a ball mill. Then 1 g of the pre-blend, 1 g of salbutamol sulphate and 8 g of coarse lactose (Prismalac 355-600) were mixed together in a glass vessel in a Turbula mixer at 42 rpm to create the final formulation. Size 2 capsules were filled with 20 mg of the formulation. For each test, 3 capsules were fired into a 'rapid TSI' from a Cyclohaler giving a total delivered dose of 6 mg of salbultamol sulphate per test. The additive material was selected from lithium stearate, calcium stearate, magnesium stearate, sodium stearate, sodium stearyl fumarate, leucine, lecithin and stearylamine.

(b) The method of (a) above was repeated using leucine, except that the pre-blend was mixed with the coarse lactose in a glass vessel shaken by hand.

The "rapid TSI" is a modified methodology based on a conventional TSI. In the rapid TSI the second stage of the impinger is replaced by a glass fibre filter (Gelman A/E, 76 mm). This enables the fine particle fraction of the formulation (i.e. particles with an MMAD<approx. 5 µm) to be collected on a filter for analysis. Analysis was conducted by sonicating the filter in a 0.06M NaOH solution and analysed at 295 nm on a UV spectrophotomer (Spectronic 601). The fine particle fraction corresponds substantially to the respirable fraction of the formulation.

Further details of the formulations and the % fine particle fraction estimated using the "rapid TSI" method described above are given in Table 16 below, in which SaSO, refers to salbutamol sulphate.

Segregation has not been observed in the above formulations, even those comprising 10 and 20% magnesium stearate (i.e. up to 2% in the final composition).

The above processes have been applied to a variety of active materials. When the active material is a protein, the milling may be preceded by lyophilisation (freeze drying) of the protein either pure or in combination with an additive material and/or a polymeric stabiliser. The freeze drying may make the protein more brittle and more easily milled. The milling may need to be conducted under cryogenic (cold) conditions to increase the brittleness of the material.

TABLE 16

| Additive Material ("AM") | % AM in pre-blend | % AM in formulation | Mass (mg) SaSO4 | Estimated % FPF | Pre-blend mill method |
|---|---|---|---|---|---|
| Lithium St | 2 | 0.2 | 2.549 | 42 | 30 mins |
|  |  |  | 2.763 | 46 |  |
| Calcium St | 2 | 0.2 | 2.721 | 45 | 1 hr |
|  |  |  | 2.633 | 44 |  |
| Magnesium St | 2 | 0.2 | 2.108 | 35 | 1 hr |
|  |  |  | 2.336 | 39 |  |
| Sodium St | 2 | 0.2 | 3.218 | 54 | 30 mins |
|  |  |  | 3.153 | 53 |  |
| Sodium stearyl Fumarate | 2 | 0.2 | 2.261 | 38 | 30 mins |
|  |  |  | 2.113 | 35 |  |
| Leucine | 2 | 0.2 | 2.429 | 40 | 2 hrs |
|  |  |  | 2.066 | 34 |  |
| Leucine[12(b)] | 2 | 0.2 | 2.136 | 36 | 2 hrs |
|  |  |  | 2.600 | 43 |  |
| Leucine | 5 | 0.5 | 2.782 | 46 | 30 mins |
|  |  |  | 3.000 | 50 |  |
| Leucine | 5 | 0.5 | 2.772 | 46 | 5 hrs |
|  |  |  | 2.921 | 49 |  |
| Magnesium St | 5 | 0.5 | 2.438 | 41 | 30 mins |
|  |  |  | 2.721 | 45 |  |
| Lecithin | 2 | 0.2 | 3.014 | 50 | 30 mins |
|  |  |  | 2.884 | 48 |  |
| Stearylamine | 2 | 0.2 | 2.847 | 47 | 30 mins |
|  |  |  | 3.037 | 51 |  |

EXAMPLE 21

10 g of the composite excipient particles containing 5% magnesium stearate obtained in accordance with Example 19 were mixed with 89.5 g coarse lactose (Prismalac; 355-600 Rm fraction) in a Turbula mixer for 30 minutes. 0.5 g micronised dihydroergotamine mesylate was added and mixing continued in the Turbula for a further 30 minutes. The powder was fired from a Cyclohaler into a MultiStage Liquid Impinger (Apparatus C, European Pharmacopoeia, Method 5.2.9.18, Supplement 2000), and gave a fine particle fraction (<approx. 5µ) of about 60%.

EXAMPLE 22

Composite excipient particles were manufactured by milling 95 g fine lactose (Sorbolac 400-Meggle) with 5 g magnesium stearate and 50 ml dichloromethane in a Retsch 5100 centrifugal mill with 620 g of 5 mm stainless steel balls in a stainless steel vessel for 90 minutes at 500 rpm. The powder was recovered after evaporation of the dichloromethane by briefly milling (1 minute) and subsequent sieving. 10 g of the composite excipient/additive particles so obtained were added to 89.5 g of sieve fractionated Prismalac Lactose (355-600 µm fraction). The mixture was tumbled in a Turbula mixer for 30 minutes at 60 rpm, then 0.5 g fentanyl citrate was added and tumbling continued for a further 30 minutes at 60 rpm. The powder so obtained was fired from a Cyclohaler at 60 l/min into a Twin-Stage Impinger, and gave a fine particle fraction (<approx. 5 µm) of about 50%.

EXAMPLE 23

Various formulations, each combining 89.5 g Prismalac log composite excipient particles and 0.5 g budesonide according to the method of Example 19. Their flowabilities were then measured using a FLODEX (trade mark) tester, made by Hanson Research. The FLODEX provides an index, over a scale of 4 to 40 mm, of flowability of powders. Analysis was conducted by placing 50 g of formulation into the holding chamber of the FLODEX via a funnel, allowing the formulation to stand for 1 minutes, and then releasing the trap door of the FLODEX to open an orifice at the base of the holding chamber. Orifice diameters of 4 to 34 mm were used to measure the index of flowability. The flowability of a given formulation is determined as the smallest orifice diameter through which flow of the formulation is smooth. The results are shown in Table 17. Comparison data is given for a formulation made by mixing for 30 minutes in a Turbula mixer 45 g Pharmatose 325M lactose (a lactose used in certain conventional formulations) and 5 g microfine lactose.

TABLE 17

| Carrier particles | Composite particles | Flowability |
|---|---|---|
| Prismalac 355-600 | Leucine:Sorbolac400 1:9 | <4 mm |
| Prismalac 355-600 | Leucine:Sorbolac400 1:9 | <4 mm |
| Prismalac 355-600 | Magnesium stearate: Sorbolac400 1:19 | <4 mm |
| Prismalac 355-600 | Magnesium stearate: microfine lactose 1:19 | <4 mm |
| Pharmatose 325M | Microfine lactose | >34 mm |

The results in Table 17 illustrate the excellent flowability of formulations using fissured lactose.

COMPARISON EXAMPLE 1

99.5 g of sieve-fractionated Prismalac (355-600 µm fraction) was tumbled with 0.5 g budesonide for 30 minutes at 60 rpm. The powder, fired from a Cyclohaler at 90 liters per minute into a Multi-Stage Liquid Impinger gave a fine particle fraction (<5 µm) of about 30%.

The invention claimed is:

1. A powder for use in a dry powder inhaler, the powder comprising:
   i) a fraction of fine particle size constituted of a mixture prepared by co-micronising a physiologically acceptable excipient and an additive, the mixture having a mean particle size of less than 35 µm;
   ii) a fraction of coarse particles constituted of a physiologically acceptable carrier having a diameter of at least 100 µm; and
   iii) at least one active ingredient having a particle size of less than 10 µm;
   said mixture (i) being composed of up to 99% by weight of particles of the physiologically acceptable excipient and at least 1% by weight of additive and a ratio between the fine excipient particles and the coarse particles being between 1:99 and 40:60% by weight, and wherein the additive partially coats the surfaces of both the physiologically acceptable excipient and the coarse particles.

2. A powder according to claim 1, which is in the form of 'hard pellets', which are spherical or semi-spherical units whose core is made of coarse particles.

3. A powder according to claim 1, wherein the mixture (i) is composed of from 90 to 99% by weight of the physiologically acceptable excipient and from 1 to 10% by weight of the additive.

4. A powder according to claim 2, wherein the mixture (i) is composed of from 90 to 99% by weight of the physiologically acceptable excipient and from 1 to 10% by weight of the additive.

5. A powder according to any one of claim 1-3 or 4, wherein the ratio between the fraction of fine particle size and the fraction of coarse particles is at least 10:90.

6. A powder according to any one of claim 1-3 or 4, wherein the ratio between the fraction of fine particle size and the fraction of coarse particles is comprised between 15:85 and 30:70% by weight.

7. A powder according to any one of claim 1-3 or 4, wherein the fraction of coarse particles is constituted of a physiologically acceptable excipient which has a particle size of 100 to 400 µm.

8. A powder according to any one of claim 1-3 or 4, in which the particle size of the mixture (i) is less than 15 µm.

9. A powder according to any one of claim 1-3 or 4, in which the fraction of fine particle size is composed of 98% by weight of the physiologically acceptable excipient and 2% by weight of the additive and the ratio between the fraction of fine particle size and the fraction of coarse particles is 10:90% by weight.

10. A powder according to any one of claim 1-3 or 4, in which the coarse carrier particles have a tapped density of not exceeding 0.7 g/cm3.

11. A powder according to any one of claim 1-3 or 4, in which the coarse carrier particles have a bulk density as measured by mercury porosimetry of not exceeding 0.6 g/cm3.

12. A powder according to any one of claim 1-3 or 4, wherein the additive is selected from the group consisting of lubricants, antiadherents and glidants.

13. A powder according to any one of claim 1-3 or 4, wherein the additive is magnesium stearate.

14. A powder according to any one of claim 1-3 or 4, wherein the physiologically acceptable excipient is one or more crystalline sugars.

15. A powder according to any one of claim 1-3 or 4, wherein the physiologically acceptable excipient is a-lactose monohydrate.

16. A powder according to any one of claim 1-3 or 4, wherein the at least one active ingredient has a particle size less than 6 μm.

17. A powder according to any one of claim 1-3 or 4, wherein the additive is magnesium stearate and the active ingredient(s) is (are) not selected from budesonide and its epimers, formoterol, TA2005 and its stereoisomers, salts thereof, and combinations thereof.

18. A powder according to any one of claim 1-3 or 4, comprising more than 5% based on the total weight of the formulation, of particles of aerodynamic diameter less than 20 μm, the formulation having a flowability index of 12 mm or less, wherein flowability is evaluated using a FLODEX (registered trademark) tester.

19. A powder according to any one of claim 1-3 or 4, comprising more than 10% based on the total weight of the formulation, of particles of aerodynamic diameter less than 20 μm, the formulation having a flowability index of 12 mm or less, wherein flowability is evaluated using a FLODEX (registered trademark) tester.

20. A process for making a powder according to any one of claim 1-3 or 4:
- wherein step i) involves co-micronising particles of the physiologically acceptable excipient and particles of the additive so as to significantly reduce their particle size;
- wherein step ii) involves spheronising by mixing the resulting mixture with the fraction of coarse particles such that mixture particles adhere to the surface of the coarse particles; and
- wherein step iii) involves adding by mixing particles of the active ingredient to the spheronised particles from step ii).

21. A process according to claim 20 wherein step i) is carried out using a jet mill.

22. A process for making a powder according to any one of claim 1-3 or 4,
- wherein step i) involves co-micronising particles of the physiologically acceptable excipient and particles of the additive so as to significantly reduce their particle size;
- wherein step ii) involves spheronising by mixing the resulting mixture with the fraction of coarse particles such that mixture particles adhere to the surface of the coarse particles; and
- wherein step iii) involves adding by mixing particles of the active ingredient to the spheronised particles from step ii);
- wherein the additive particles at least partially coat the surface of the particles of the pharmaceutically acceptable excipient.

* * * * *